US010041939B2

(12) United States Patent
Nieuwenhuis et al.

(10) Patent No.: US 10,041,939 B2
(45) Date of Patent: Aug. 7, 2018

(54) BINDING ASSAY WITH MULTIPLE MAGNETICALLY LABELLED TRACER BINDING AGENTS

(75) Inventors: Jeroen Hans Nieuwenhuis, Eindhoven (NL); Toon Hendrik Evers, Eindhoven (NL)

(73) Assignee: Minicare B.V., Eindhoven (NL)

( * ) Notice: Subject to any disclaimer, the term of this patent is extended or adjusted under 35 U.S.C. 154(b) by 1275 days.

(21) Appl. No.: 13/497,813

(22) PCT Filed: Sep. 10, 2010

(86) PCT No.: PCT/IB2010/054094
§ 371 (c)(1), (2), (4) Date: Mar. 23, 2012

(87) PCT Pub. No.: WO2011/036597
PCT Pub. Date: Mar. 31, 2011

(65) Prior Publication Data

US 2012/0178186 A1 Jul. 12, 2012

(30) Foreign Application Priority Data

Sep. 23, 2009 (EP) .................................... 09305887

(51) Int. Cl.
*G01N 33/553* (2006.01)
*G01N 33/543* (2006.01)
*G01N 27/74* (2006.01)

(52) U.S. Cl.
CPC ..... *G01N 33/54326* (2013.01); *G01N 27/745* (2013.01)

(58) Field of Classification Search
CPC ......... G01N 33/54326; G01N 35/0098; G01N 2035/0436; B01L 2300/0816; B01L 2300/0819

(Continued)

(56) References Cited

U.S. PATENT DOCUMENTS 6,074,827 A * 6/2000 Nelson ................. G01N 33/569 435/6.1
7,303,884 B1 * 12/2007 Bertling ......................... 435/7.1
(Continued)

FOREIGN PATENT DOCUMENTS

DE 102004050838 A1 4/2006
DE 102005033643 A1 2/2007
(Continued)

OTHER PUBLICATIONS

Nieuwenhuis, Jeroen, "Magnotech: Reliable and Fast Magnetic Point-of-Care Biosensor Technology" 41st Annual Oak Ridge Conf. Apr. 16, 2009.

(Continued)

*Primary Examiner* — Ann Y Lam
(74) *Attorney, Agent, or Firm* — McCoy Russell LLP

(57) ABSTRACT

The present invention relates to a cartridge (1) for the detection of an analyte (2) in a binding assay with magnetic labels (3), the cartridge comprising at least one capture binding agent (4) against a binding site on the analyte and comprising at least two magnetically labelled tracer binding agents (51 and 52) against further different binding sites on the analyte, characterized in that the cartridge comprises at least two regions (61 and 62) wherein a first region (61) comprises the at least one capture binding agent (4) and a first magnetically labelled tracer binding agent (51) and wherein a second region (62) comprises at least one capture binding agent (4) and a second magnetically labelled tracer binding agent (52). Herein the first region (61) does not comprise a magnetically labelled tracer binding agent other than the first magnetically labelled tracer bind agent (51) and wherein the second region (62) does not comprise a magnetically labelled tracer binding agent other than the second magnetically labelled tracer binding agent (52).

4 Claims, 4 Drawing Sheets

2
51
L
52
L
4

(58) Field of Classification Search
USPC .......................................................... 436/526
See application file for complete search history.

(56) References Cited

U.S. PATENT DOCUMENTS

2003/0211797 A1 11/2003 Hill
2006/0257958 A1 11/2006 Bruno
2007/0042427 A1* 2/2007 Gerdes ............. G01N 33/54366 435/7.1
2009/0098540 A1 4/2009 Baeumner
2010/0230613 A1* 9/2010 Pieprzyk ........... B01L 3/502738 250/459.1
2010/0289483 A1* 11/2010 Immink ............. G01R 33/1269 324/204
2010/0311185 A1* 12/2010 Scheib ............. G01N 33/54306 436/501
2016/0356789 A1* 12/2016 Caffrey .............. G01N 33/6887

FOREIGN PATENT DOCUMENTS

EP 1473567 A1 11/2004
EP 2020831 A1 2/2009
JP 2003309278 A1 10/2003
WO 2002084617 A1 10/2002
WO 2005031550 A1 4/2005
WO 2007033385 A2 3/2007
WO 2008139376 A1 11/2008
WO 2009115951 A1 9/2009

OTHER PUBLICATIONS

Dittmer, W.U. et al "Sensitive and Rapid Immunoassay for Parathyroid Hormone using Magnetic Particle Labels and Magnetic Actuation" Journal of Immunological Methods, vol. 338, No. 1-2, Sep. 30, 2008, pp. 40-46.

Carpi, Federico et al "Electroactive Polymer-Based Devices for e-Textiles in Biomedicine", IEEE Transactions on Inofmration Technology in Biomedicine, vol. 9, No. 3, Sep. 2005, pp. 295-318.

Eriksson et al "Negative Interference in Cardiac Troponin I Immunoassays by Circulating Troponin Autoantibodies" Clinical Chemistry, vol. 51, p. 839-847.

* cited by examiner

BINDING ASSAY WITH MULTIPLE MAGNETICALLY LABELLED TRACER BINDING AGENTS

The present invention relates to binding assays with magnetically labelled binding agents such as antibodies.

Sandwich immunoassays are well known methods for detecting an analyte wherein typically a first antibody for the analyte is bound to a substrate of a reaction chamber (capture antibody) and where a second antibody for the same analyte (soluble or in suspension) is bound to detectable label (tracer antibody). Such detectable labels include chromophoric labels (e.g. fluorescent labels) and magnetic particles.

In such sandwich immunoassay an analyte may not be detected when one of the antibodies does not bind to the analyte. This can be caused, for example, by degradation of the analyte (e.g. proteolysis), a change in an epitope on the analyte (e.g. (de)phosphorylation) or complex formation with other proteins which shield an epitope on the analyte from binding to the antibody. The above phenomena may lead to false negative results in the detection of disease markers.

Troponin is a well-established marker for a variety of heart disorder. This protein however, forms different subunits and is easily degraded after the collection of a blood sample. In order to address this problem, assays have been developed wherein two different tracer antibodies are used [Eriksson et al. (2006) *Clin. Chem.* 51, 839-847; European patent application EPP1473567] [FIG. 1]. In this type of prior art assays, the tracer antibodies are labelled with fluorescent small organic molecules.

Performing such assays with magnetic labels provides unforeseen problems. The binding of two magnetically labelled tracer antibodies to an analyte (so-called bridging) makes it difficult for the analyte to further bind to a capture antibody [FIG. 2] due to steric hindrance caused by the relatively large size of the magnetic particles compared to the size of protein analyte.

Further adaptations are required to perform sandwich assays with different magnetically labelled tracer antibodies.

Particular and preferred aspects of the invention are set out in the accompanying independent and dependent claims. Features from the dependent claims may be combined with features of the independent claims and with features of other dependent claims as appropriate and not merely as explicitly set out in the claims.

The present invention prevents false negative results wherein disease markers, which are present in a sample, would not be detected and a person with a disorder or at risk for a disorder would be considered healthy.

One aspect of the present invention relates to a cartridge (1) for the detection of an analyte (2) in a binding assay with magnetic labels (3), the cartridge comprising at least one capture binding agent (4) against a binding site on the analyte and comprising at least two magnetically labelled tracer binding agents (51 and 52) against further different binding sites on the analyte, characterised in that the cartridge comprises at least two regions (61 and 62) wherein a first region (61) comprises the at least one capture binding agent (4) and a first magnetically labelled tracer binding agent (51) and wherein a second region (62) comprises at least one capture binding agent (4) and a second magnetically labelled tracer binding agent (52). Herein the first region (61) does not comprise a magnetically labelled tracer binding agent other than the first magnetically labelled tracer bind agent (51) and wherein the second region (62) does not comprise a magnetically labelled tracer binding agent other than the second magnetically labelled tracer binding agent (52).

According to particular embodiments of cartridges described herein these comprise two capture binding agents (41 and 42) against two different binding sites on the analyte, wherein the first region (61) contains the first capture binding agent (41), and wherein the second region (62) contains the second capture binding agent (42).

According to other particular embodiments of cartridges described herein these comprise two capture binding agents (41 and 42) against two different binding sites on the analyte, wherein the first region (61) contains the first capture binding agent (41) and the first tracer binding agent (51), and wherein the second region (62) contains the second capture binding agent (42) and the second tracer binding agent (52).

According to other particular embodiments of cartridges described herein these comprise two capture binding agents (41 and 42) against two different binding sites on the analyte, wherein both the first region (61) and the second region (62) comprise the first capture binding agent (41) and the second capture binding agent (42).

According to yet other particular embodiments of cartridges described herein these comprise two capture binding agent (41 and 42) against two different binding sites on the analyte and comprising two magnetically labelled tracer binding agent (51 and 52) against a further two different binding sites on the analyte, wherein the cartridge comprises two regions (61 and 62) wherein a first region (61) comprises the first and second capture binding agent (41 and 42) and the first magnetically labelled tracer binding agent (51) and wherein the second region (62) comprises the first second and second capture binding agent (41 and 42) and the second magnetically labelled tracer binding agent (52).

According to other particular embodiments of cartridges described herein binding agents are antibodies.

According to other particular embodiments of cartridges described herein a region is a reaction chamber.

According to other particular embodiments of cartridges described herein the analyte is Troponin, such as cardiac Troponin I (cTnI).

Another aspect of the invention relates to a method of detecting an analyte (2) in a sample with a binding assay using magnetically labelled tracer binding agents, the method comprising the steps of:

a) providing a cartridge (2) with at least two regions (61 and 62), wherein a capture binding agent (4) against an binding site on the analyte is immobilised on a surface of the regions (61 and 62),
b) providing in the first region (61) a complex of the analyte with a magnetically labelled first tracer binding agent against a further binding site on the analyte (51),
c) providing in the second region (62) a complex of the analyte with a magnetically labelled second tracer binding agent (52) against a yet further binding site on the analyte,
d) allowing the binding of the complex of step b) and c) with the capture binding agents in the regions,
e) detecting the binding of the complex of step b) and c) to the capture binding agent, wherein in the method the first region (61) does not comprise a magnetically labelled tracer binding agent other than the first magnetically labelled tracer binding agent (51) and the second region (62) does not comprise a magnetically labelled tracer binding agent other than the second magnetically labelled tracer binding agent (52).

According to other particular embodiments of methods described herein tracer binding agents are provided in the region prior to the introduction of the liquid comprising the analyte.

According to other particular embodiments of methods described herein binding agents are antibodies.

According to other particular embodiments of methods described herein a region is a reaction chamber.

According to further particular embodiments of methods described herein the analyte is Troponin, such as cardiac Troponin I (cTnI) wherein a tracer antibody (41) and a capture antibody (51) bind to different epitopes on the stable region of cTnI, and, wherein a tracer antibody (42) and a capture antibody (52) bind to different epitopes on the unstable region of Troponin.

A further aspect of the invention relates to a device for performing a binding assay using magnetic actuation, comprising the cartridge as described above.

Another aspect of the present invention relates to a kit comprising at least three different binding agents binding to different binding site on a same analyte, wherein at least two of the binding agents are labelled with a magnetic particle, and wherein at least one of the binding agents is not labelled with a magnetic particle.

According to particular embodiments of kits described herein kits comprise four different binding agents binding to four different binding sites on a same analyte, wherein two of the four binding agents are labelled with a magnetic particle.

According to further particular embodiments of kits described herein, the binding agents are antibodies.

According to particular embodiments of kits described herein, the analyte is Troponin, According to particular embodiments of kits described herein, the analyte is cardiac Troponin I, and the first unlabelled and the first magnetically labelled antibody bind to different epitopes on the stable region of cardiac Troponin I, and, the second unlabelled and the second magnetically labelled antibody bind to different epitopes on the unstable region of cardiac Troponin I.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

FIG. 1 shows a schematic overview of a prior art immunoassay. One capture antibody (4) and two different tracer antibodies (51, 52) bind the analyte (2). The stars (L) represent fluorescent labels.

Figure 1:
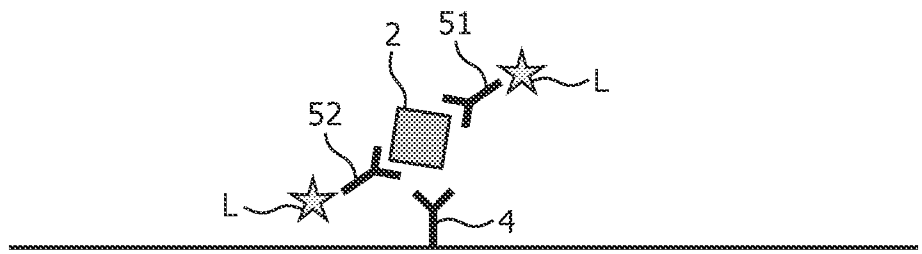

In the different figures, the same reference signs refer to the same or analogous elements. Whereas the figures provide particular embodiments where the binding agents are antibodies, the elements (4), (41), (42), (5), equally refer to other binding agents as further detailed in the present invention.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. These definitions should not be construed to have a scope less than understood by a person of ordinary skill in the art.

"Region" in the context of the present invention refers to a part of a reaction chamber or to an entire reaction chamber where a magnetically labelled tracer binding agent is present during the interaction of the analyte/tracer binding agent complex and the capture binding agent.

"Reaction chamber" in the context of the present invention relates to a part of a device or cartridge wherein the formation of a complex between a tracer binding agent (typically an antibody), an analyte, and a capture binding agent (typically an antibody) takes places. The portion of the reaction chamber where the capture binding agent is immobilised is referred to as "reaction surface". The reaction chamber is typically a portion of a channel between the sample application zone (inlet) and the outlet, such as a widened part of a capillary tubing. Generally, the reaction chamber has at least one flat surface to which capture binding agents are immobilised. Apart from the formation of the above complex, the reaction chamber is mostly also used for detecting the formation of such complexes and functions then also as "detection chamber". When optical means are used for the detection, the reaction chamber contains at least one light transparent portion. For most commercial applications, reaction chambers are integrated in a cartridge which is a unit which can inserted in a device which comprises capillary tubing, to deliver and remove sample fluid, washing fluid and buffer fluids. The cartridge typically also comprises items, such as dried reagents (lysing agents) and buffers and a filter to remove particulate matter from a sample. A cartridge as used in the present invention comprises at least one reaction chamber with separate regions or at least two separate reaction chambers. When one reaction chamber with different zones is used separate means that a tracer binding agent (typically an antibody) can not be manipulated from one zone in the reaction chamber into another zone in the reaction chamber. When one reaction chamber with different zones is used "separate" means that a tracer binding agent (typically an antibody) can not be manipulated from one reaction chamber into the other reaction chamber.

Nevertheless, a reaction chamber can be used for multiplexing assays wherein different tracer binding agents for different analytes are positioned at different reaction surfaces, with the proviso that different tracer binding agents (51, 52) for different binding sites on the same analyte as described in the present invention are not within the same region when one reaction chamber is used or are not within the same reaction chamber if different reaction chambers are used.

"Sandwich assay" refers to a well-known type of binding assay, wherein an analyte is immobilised to a surface via an antibody against a first epitope of the analyte and is detected with an antibody against a second epitope of this analyte, wherein this second antibody carries a detectable label.

"Binding agent" relates to a moiety which specifically binds with a part of an analyte. A typical example is an antibody or a fragment thereof (Fab, Fab(2), scFv) binding to an epitope of a protein. Such antibody is typically a monoclonal antibody, although a polyclonal antibody raised against an epitope is equally suitable. Other examples of binding agents are aptamers, nanobodies, affibodies anticalins; carbohydrate binding protein such as lectins for binding to carbohydrate analytes; carbohydrates for binding to carbohydrate binding protein analytes; oligo- or polynucleotides for binding to DNA- or RNA-binding proteins; organic molecules (such as enzyme substrates or enzyme inhibitors, ligands or antagonists of a receptor) binding to protein analytes; peptides, proteins or parts thereof binding to other peptides or proteins (such as parts of multi protein complexes, or protein ligand receptor complexes)

"Analyte" in the context of the present invention relates to a compound which can be detected via the binding of a binding agent to a binding site on the analyte. The analyte is typically a protein wherein the binding site is an epitope of said protein which binds to an antibody. The protein analyte can be a single polypeptide but can also be a complex of different polypeptides. Accordingly, assays as described herein comprise tests for multi-subunit protein complexes wherein binding agents such as antibodies bind on binding sites (epitopes in the case of antibody/protein binding) residing on different subunits of such complex. Other analytes include, carbohydrates, complex organic molecules such as enzyme inhibitors, receptor binding agents, hormones, pharmaceutical compounds, "Magnetic label" refers to a particle consisting of or comprising magnetic or magnetisable material of any shape, typically spherical, which can be manipulated by a magnetic field.

The size of magnetic particles with a diameter between about 50 to 2000 nm, particularly between about 250 and 750 nm and more particularly around 500 nm, which are typically used in immunoassays may lead to unforeseen problems in binding assays with two or more tracer binding agents such as antibodies which are labelled with magnetic particles. In a sandwich assay, a tracer antibody first binds with the analyte whereafter the complex between the analyte and tracer antibody is brought into contact with the immobilised capture antibody. This procedure is also followed in magnetic particle based assays. Herein the tracer antibodies are manipulated by magnetic stirring to allow binding of the tracer antibody with the analyte. Hereafter the complex between the analyte and the tracer antibody is manipulated towards the capture antibodies on the detection. Afterwards, tracer antibodies without analyte are removed by applying a magnetic field away from the capture antibodies. The detection of the analyte takes place at the surface wherein the capture antibodies are immobilised.

The number of bound particles is related to the amount of analyte molecules present in the sample.

The use of two different tracer binding agents such as antibodies each labelled with a magnetic particle, results in a complex of an analyte molecule being positioned between two magnetic particles. The size of such magnetic particles may prevent the binding of the analyte to the capture binding agent. If such binding does not occur also the analyte-tracer binding agent complex will be pulled away form the capture binding agents at the end of the assay and the analyte, although present in the sample will not be detected.

Figure 2:
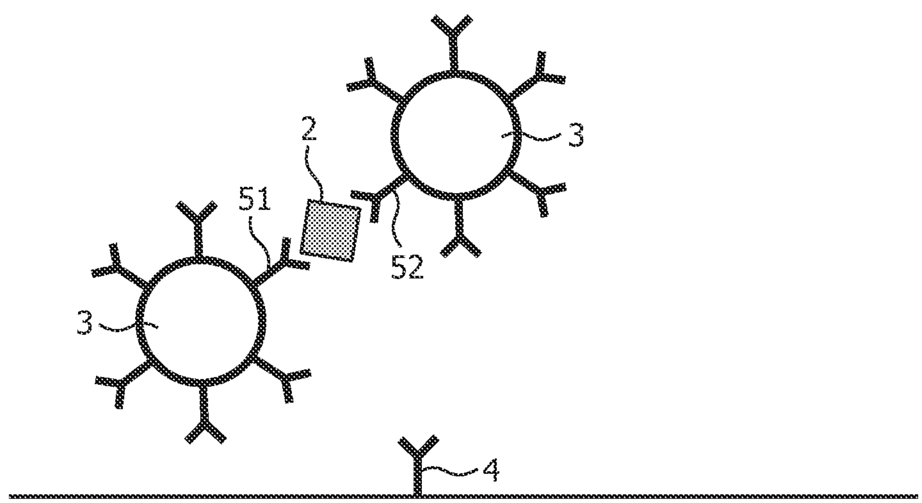
FIG. 2 shows a schematic overview of the steric hindrance encountered when replacing, in an assay as depicted in FIG. 1, small fluorescent labels by large magnetic particles (3).

The methods and cartridges of the present invention solve this problem by performing in parallel within the same device different binding assays such sandwich assays wherein in each assay only one type of magnetically labelled tracer binding agent (typically an antibody) is used. Typical embodiments refer to cartridges and methods wherein four different antibodies each against a different epitope are used for the detection of an analyte, of which two antibodies are used as capture antibodies which are both immobilised in each of two reaction chambers and two antibodies are used as magnetically labelled tracer antibodies, wherein each reaction chamber comprises one of the two capture antibodies. This concept can be broadened, as long as:

- at least one capture binding agent is used, and,
- at least separated regions with capture binding agents are present in a cartridge, and (as two separate reaction chambers or as one reaction chamber with separate regions),
- at least two magnetically labelled tracer binding agents are used, whereby in each region only one type of magnetically labelled binding agent is used such that e.g. an analyte molecule can never bind via two different epitopes to antibodies with magnetic labels as depicted in FIG. 2.

Thus in the broadest sense, a first aspect of the invention relates to a cartridge (1) for the detection of an analyte (2) in a binding assay with magnetic labels (3), said cartridge comprising at least one capture binding agent (4) against an binding site for said analyte and comprising at least two magnetically labelled tracer binding agents (51 and 52) against further different binding sites for said analyte, characterised in that said cartridge comprises at least two reaction chambers (61 and 62) wherein a first reaction chamber (61) comprises said at least one capture binding agent (4) and a first magnetically labelled tracer (51) and wherein a second reaction chamber (62) comprises said at least one capture binding agent (4) and a second magnetically labelled tracer binding agent (52). The first regions (61) does not comprise a magnetically labelled tracer binding agent other than the first magnetically labelled tracer binding agent (51)

and the second region (62) does not comprise a magnetically labelled tracer binding agent other than the second magnetically labelled tracer binding agent (52).

Figure 3:
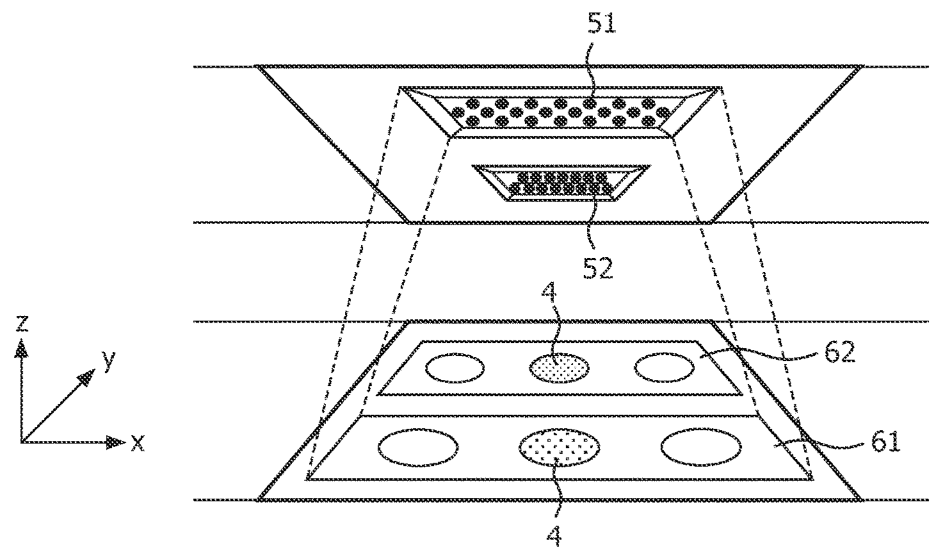
FIG. 3 shows an exemplary embodiment of a cartridge (1) according to the present invention with two zone (61, 62), one capture antibody (4) and two magnetically labelled tracer antibodies (51 and 52). Herein magnetically labelled tracer antibodies (51 and 52) are manipulated up and down in a perpendicular direction along axis Z to the capture antibody (4) on respectively region (61) and (62).
Figure 4:
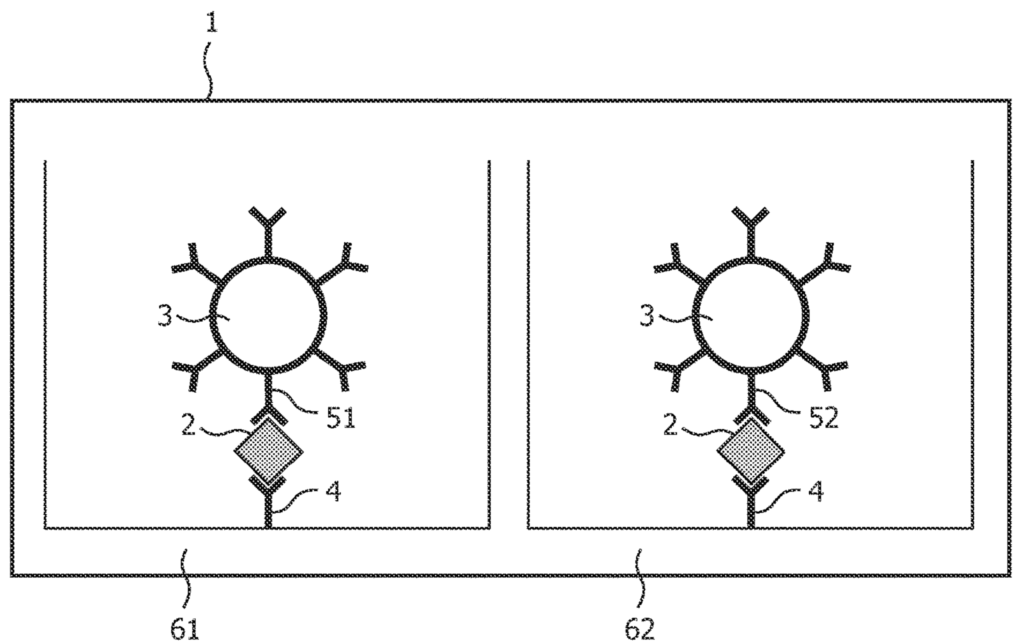
FIG. 4 shows an exemplary embodiment of a cartridge (1) according to the present invention with two reaction chambers (61, 62), one capture antibody (4) and two tracer antibodies (51 and 52) attached to magnetic particles (3) for the detection of analyte (2).

Cartridges and methods as described in the present invention can be performed in one and the same reaction chamber, when dedicated regions are created such that an interaction of an analyte molecule with both tracer binding agent (51) and (52), leading to the undesirable bridging complex as depicted in FIG. 2 is avoided. This is illustrated with an example in FIG. 3, wherein magnetically labelled tracer binding agents are applied and dried on separate regions of a cartridge. As soon as liquid enters the cartridge and the magnetic particles are resuspended, a magnetic field is applied that either keeps the magnetic particles immobilised or manipulates the magnetic particles in an essentially perpendicular direction (indicated by the arrow z in FIG. 3) towards and away from the capture binding agents on the opposite side in the cartridge. The perpendicular manipulation of the magnetic particles avoids that magnetically labelled tracer binding agent (51) and (52) come into contact which other and avoids that an analyte bound to magnetically labelled tracer binding agent (51) can further bind to magnetically labelled tracer binding agent (52) and vice versa.

In a particular embodiment said regions (61) and (62) are individual reaction chambers.

In another particular embodiment said binding agents are antibodies.

The further details of such a cartridge will be illustrated with an embodiment wherein the cartridge comprises two reaction chambers (61 and 62) with two capture antibodies (41 and 42) against two different epitopes for the analyte and two tracer antibodies (51 and 51) with magnetic labels against two further epitopes of said analyte.

The capture antibodies are immobilised to a surface of the reaction chamber using techniques known in the art for the immobilisation of proteins to surfaces such as plastic, glass, ceramics and metal. In particular embodiments, the binding between the reaction surface and the capture antibody may be reversible using e.g. thiol sensitive linkers.

The cartridge further comprises two magnetically labelled tracer antibodies (51 and 52) against a further two different epitopes for said analyte. Methods to bind proteins to magnetic particles are well known in the art. Generally, one magnetic particle will carry different antibody molecules to its surface, but reaction conditions can be adapted to control the number of antibodies that bind to a single particle, to obtain eventually a ratio of one antibody per particle. Different types of magnetic particles have been described in the prior art, varying in shape and material. Typically, magnetic particles with a diameter between about 50 to 2000 nm, particularly between about 250 and 750 nm and more particularly around 500 nm are used for methods as described in the present invention. The magnetic particles are in first instance used to manipulate the attached tracer antibodies in a magnetic field. Optionally, the magnetic properties of a particle can also be used to detect the particles. Alternatively, the detection of magnetic particles is based on optical properties such as the size of the particle itself (e.g. as measured in FTIR (Frustrated Total Internal Reflection)) or by adding chromophoric groups to the magnetic particle (e.g. a fluorescent polystyrene particle comprising magnetic material).

The cartridge comprises two reaction chambers (61 and 62) for the detection of the analyte (2). Nevertheless, the cartridge can contain further reaction chambers for the detection of other analytes. The first reaction chamber (61) comprises said two capture antibodies (41 and 42) against different epitopes for the analyte and a first magnetically labelled tracer antibody (51) binding to a further (third) epitope on the antibody. The second reaction chamber (62) comprises the above mentioned two capture antibodies (41 and 42) and a second magnetically labelled tracer antibody (52) binding to yet a further (fourth) epitope on the antibody.

The tracer antibodies are in particular embodiments applied in the reaction chamber prior to the use of the cartridge. For example, the tracer antibodies are applied in a buffer on a part of the reaction chamber remote from the capture antibodies and are dried. Upon introduction of the sample liquid in the reaction buffer, the tracer antibodies are dissolved or redispersed.

In alternative embodiments, the tracer antibodies are contacted with the sample prior to the entry of the sample into the reaction chamber. Typically this occurs when the tracer antibodies are supplied in a channel between the sample inlet and the reaction chamber. It is apparent that in such a configuration, the channels are designed in such a way that one type of tracer antibody can only migrate into one reaction chamber. The tracer antibodies will be solubilised when the sample with the analyte enters the channel and will then enter the reaction chamber as a complex with the analyte, or if all analyte is bound, or no analyte is present as tracer antibody as such.

In the above described cartridge, bridging complexes of an analyte with two different antibodies each bound to a magnetic particle will not occur. An analyte molecule will only one carry magnetic particle.

Devices and methods as described in the present invention are applicable to any type of analyte that require the use of different tracer binding agent. The reasons why different tracer binding agents such as antibodies are required may differ and include differences in post-translational modifications (e.g. phosphorylation, glycosylation), proteolytic degradation or processing, complex formation with other components which prevent binding of a tracer binding agent such as antibody to an analyte, and conformational changes in an epitope of an analyte.

In particular embodiments the analyte is Troponin. This protein is a multimeric protein that at the one hand is involved in the formation of different complexes which may shield an epitope from an antibody and which at the other hand is prone to proteolytic degradation after the collection of a blood sample. The presence of cardiac Troponin-I (cTnI) and cardiac Troponin-T (cTnT) in the blood is indicative for cardiac cell death and is used in the diagnosis of acute myocardial infarction (AMI), unstable angina, post-surgery myocardium trauma and other diseases related with cardiac muscle injury.

Figure 7:
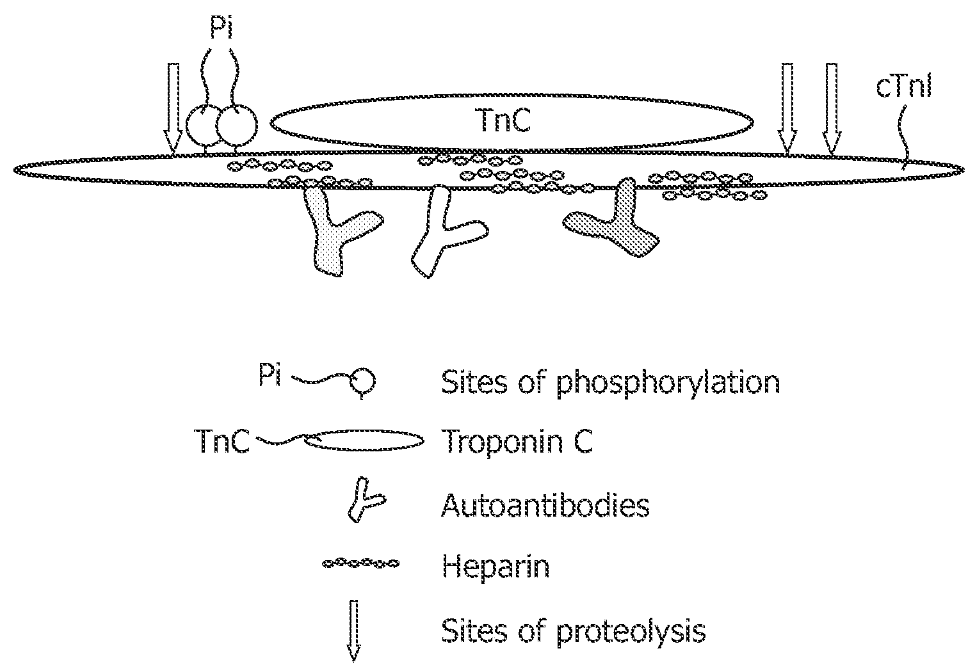
FIG. 7 shows a schematic structure of a Troponin C/Troponin I complex (taken from Hytest catalogue (Hytest, Turku, Finland)).

The structure of cardiac Troponin-I (cTnI) is shown in FIG. 7. The middle part (AA 30-109) of the molecule is quite stable, but there is the chance that auto-antibodies bind to the molecule. Some other sites of the molecule can be blocked by heparin (an anti-coagulant) that may be present in a blood sample. The outermost regions (AA 1-29 and AA 110-209) of the molecules show less interference, but these tend to be less stable and can be cut off under certain circumstances. Antibody binding can further be influenced by differences in phosphorylation on Ser22 and Ser23 or differences in the oxidation state of Cys80 and Cys97. All these modifications to the TcnI analyte can prevent binding by the tracer antibody on the particle and therefore lead to an incorrect test result, whereas the use of different tracer antibodies with magnetic particles binding to Troponin in one and the same reaction chamber may generate the bridging problem described above and prevent binding of the analyte to the capture antibody leading to false negative results. The use of different magnetically labelled tracer antibodies in separate reaction chambers solves this problem.

Another aspect of the invention relates to a method of detecting an analyte (2) in a sample with a binding assay using magnetically labelled tracer binding agents. This method comprises the steps of:

a) providing a cartridge (1) with at least two regions (61 and 62), wherein a capture binding agent (4) against an binding site for said analyte is immobilised on a surface of said regions (61 and 62), b) providing in said first region (61) a complex of the analyte with a magnetically labelled first tracer binding agent against a further binding site of said analyte (51), c) providing in said second region (62) a complex of the analyte with a magnetically labelled second tracer binding agent (52) against a yet further epitope of said analyte, d) allowing the binding of the complex of step b) and c) with the capture binding agent (4) in said regions, e) detecting the binding of the complex of step b) and c) to the capture binding agents, wherein in said method the first region (61) does not comprise a magnetically labelled tracer binding agent other than the first magnetically labelled tracer binding agent (51) and the second region (62) does not comprise a magnetically labelled tracer binding agent other than the second magnetically labelled tracer binding agent (52).

In a particular embodiment said regions (61) and (62) are reaction chambers.

In another particular embodiment said binding agents are antibodies.

As explained above for the cartridge, the method will be described in detail for an embodiment wherein two different capture antibodies (41 and 42) and two different magnetically labelled tracer antibodies (51 and 52) are used. This method comprises the following steps:

providing a cartridge (1) with two reaction chambers (61 and 62), wherein two capture antibodies (41 and 42) against two different epitopes for said analyte are immobilised on a surface of said reaction chambers (61 and 62). The details of this reaction chamber are described above. Methods to apply and immobilise antibodies to a surface are well known in the art.

providing in said first reaction chamber (61) a complex of the analyte with a magnetically labelled first tracer antibody (51), and providing in said second reaction chamber (62) a complex of the analyte with a magnetically labelled second tracer antibody (52). Such complex may be formed outside the reaction chamber, e.g. upon processing of a sample or by providing the tracer antibody in a fluidic channel between the sample application and the reaction chamber. In particular embodiments, tracer antibodies are applied within the reaction during the manufacture of a cartridge, such that a complex with the analyte can be formed upon introduction of sample liquid into the reaction chamber. The formation of the complex is facilitated by magnetic actuation of the particles.

allowing the binding of the complex of step b) and c) with the capture antibodies in said reaction chambers. During or after the above mentioned actuation magnetic particles are manipulated towards the surface where the capture antibodies are located. At the end of this binding step, a magnetic field is applied directed away from the capture antibodies to remove unbound tracer antibodies.

detecting the binding of the tracer antibody and the analyte to the capture antibodies. This detection can be done by measuring a detectable property of the particles, such as detecting the magnetic of electrical properties of the magnetic material, detecting the presence of a particle using optical techniques such as light scattering, more particularly FTIR, or detecting the presence of a chromophoric group (e.g. fluorescence) which may be present within the magnetic particle. The detection typically takes places within the reaction chamber on the surface where the capture antibodies are immobilised. Alternative embodiments are however envisaged whereby the magnetic particles are collected and measured outside the reaction chamber (for example after denaturing conditions or conditions wherein e.g. the binding of the capture antibody to the surface involves a disulfide bridge which is reduced.

The above method can be adapted to include modifications of sandwich assays, microfluidic devices, actuation methods, and detection method, with the proviso that in methods in accordance with the present invention, the first region (61) does not comprise the magnetically labelled second tracer antibody (52) and wherein the second region (62) does not comprise the magnetically labelled first tracer antibody (51).

The implementation in a biosensor can be transparent to the user, the signals from both chambers or regions can be combined using an algorithm and only the final results can be displayed to the user.

Other arrangements of the systems and methods embodying the invention will be obvious for those skilled in the art.

It is to be understood that although preferred embodiments, specific constructions and configurations, as well as materials, have been discussed herein for devices according to the present invention, various changes or modifications in form and detail may be made without departing from the scope and spirit of this invention.

EXAMPLES

Example 1. Detection of Cardiac Troponin I (cTnI)

Figure 5:
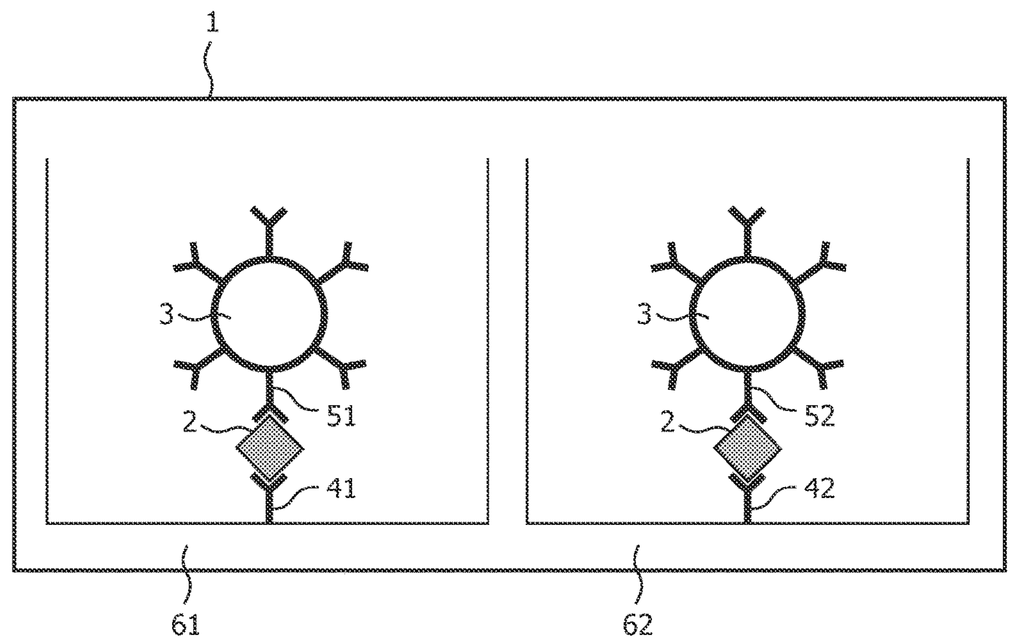
FIG. 5 shows an exemplary embodiment of a cartridge (1) according to the present invention with two reaction chambers (61, 62), two capture antibody (41 and 42) and two tracer antibodies (51 and 52) attached to magnetic particles (3) for the detection of analyte (2).
Figure 6:
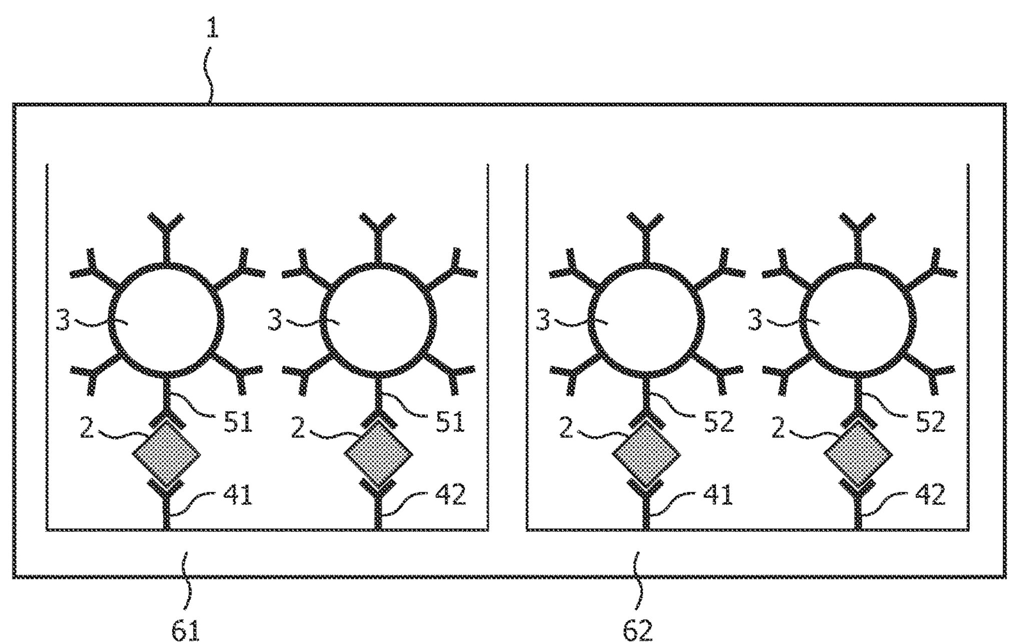
FIG. 6 shows an exemplary embodiment of a cartridge (1) according to the present invention with two reaction chambers (61, 62), two capture antibodies (41 ad 42) and two tracer antibodies (51 and 52) attached to magnetic particles (3) for the detection of analyte (2).

The principle of the method described in the present inventions is illustrated below for the case of cTnI where two antibodies against the stable [S] region (Ab-S1 (51) and AbS2 (41)) and two antibodies against the unstable [US] region of the molecule (US-Ab1 (52) and US-Ab2 (42)) are used. In each reaction chamber only tracer antibodies are present that bind to one epitope of the target molecule, hence complexes of the analyte molecule with two magnetic particles cannot occur. Since on the surface of the sensor both capture antibodies against the stable and against the unstable part of the molecule are present, this assay still has robust properties. In case auto-antibodies are present (which block the binding sites of the stable part of the molecule) particles in the chamber can still bind to the US-Ab2 (42) on the sensor surface. In case the less stable regions of the molecule are not available, tracer antibodies in chamber can still bind. In the format as depicted in FIG. 5 the reaction surface contains a combination of both types of capture antibodies.

The volume of a blood sample (about 20 μl) used in a magnetic label assay is large enough to split a sample over 2 chambers without additional measures to perform this assay.

In the different chambers multiplexing can be performed with other magnetic particles that have antibodies against other targets, since bridging between those particles is not possible.

A variety of antibodies for C Troponin I is commercially available from e.g. Hytest, Finland. Combination of two capture antibodies and two tracer antibodies, have been described by Hytest and include the following combinations.

| capture antibodies (41, 42) | tracer antibody (51, 52) |
|---|---|
| $Ab_{90-196} + Ab_{83-93}$ | $Ab_{41-49} + Ab_{169-178}$ |
| $Ab_{18-28} + Ab_{83-93}$ | $Ab_{41-49} + Ab_{83-93}$ |
| $Ab_{18-28}$, $Ab_{83-93}$ | $Ab_{41-49} + Ab_{169-178}$ |

The numbers in subscript refer to the epitope of cTnI.

The invention claimed is:

1. A cartridge for the detection of analyte cardiac Troponin I (cTnI) in a binding assay with magnetic labels, the cartridge comprising:

at least one immobilized capture binding agent against a binding site on the analyte;

at least two magnetically labeled tracer binding agents against binding sites on the analyte different from the binding site of the capture binding agents;

a first reaction chamber comprising a portion of a first channel between a first analyte inlet zone and a first analyte outlet zone of the first channel, and comprising the at least one immobilized capture binding agent and a first magnetically labeled tracer binding agent, wherein the first magnetically labeled tracer binding agent is solubilized when the analyte enters the first channel and enters the reaction chamber as a complex with the analyte, and a second reaction chamber comprising a portion of a second channel between a second analyte inlet zone and a second analyte outlet zone of the second channel, and comprising the at least one immobilized capture binding agent and a second magnetically labeled tracer binding agent, wherein the second magnetically labeled tracer binding agent is solubilized when the analyte enters the second channel and enters the reaction chamber as a complex with the analyte;

wherein the first and second reaction chambers are not in fluid communication, and wherein the first magnetically labeled tracer binding agent is supplied in the first channel between the first analyte inlet zone and the first reaction chamber, and the second magnetically labeled tracer binding agent is supplied in the second channel between the second analyte inlet zone and the second reaction chamber;

wherein the first reaction chamber does not comprise a magnetically labeled tracer binding agent other than the first magnetically labeled tracer binding agent;

wherein the second reaction chamber does not comprise a magnetically labeled tracer binding agent other than the second magnetically labeled tracer binding agent;

wherein bridging complexes of an analyte with two different capture binding agents each bound to a magnetic particle do not form in the cartridge; and wherein when the different capture binding agents are $Ab_{90-196}$ and $Ab_{83-93}$ of cTnI, then the first and second magnetically labeled tracer binding agents are $Ab_{41-49}$ and $Ab_{169-178}$ of cTnI; or when the different capture binding agents are $Ab_{18-28}$ and $Ab_{83-93}$ of cTnI, then the first and second magnetically labeled tracer binding agents are $Ab_{41-49}$ and $Ab_{83-93}$ of cTnI; or when the different capture binding agents are $Ab_{18-28}$ and $Ab_{83-93}$ of cTnI, then the first and second magnetically labeled tracer binding agents are $Ab_{41-49}$ and $Ab_{169-178}$ of cTnI.

2. The cartridge according to claim 1, wherein the at least one immobilized capture binding agent against a binding site on the analyte comprises:

first and second capture binding agents against two different binding sites on the analyte;

wherein the first reaction chamber contains the first capture binding agent and the first tracer binding agent; and wherein the second reaction chamber contains the second capture binding agent and the second tracer binding agent.

3. The cartridge according to claim 2, wherein each of the first and second reaction chambers comprises the first and second capture binding agents.

4. The cartridge according to claim 1, wherein each of said binding agents is an antibody.

* * * * *